US009234840B2

(12) United States Patent
Brezinski

(10) Patent No.: US 9,234,840 B2
(45) Date of Patent: Jan. 12, 2016

(54) DETERMINATION OF A MATERIAL CHARACTERISTIC WITH THE USE OF SECOND-ORDER PHOTON CORRELATION

(76) Inventor: Mark Brezinski, Marblehead, MA (US)

(*) Notice: Subject to any disclaimer, the term of this patent is extended or adjusted under 35 U.S.C. 154(b) by 229 days.

(21) Appl. No.: 14/006,463

(22) PCT Filed: Mar. 22, 2012

(86) PCT No.: PCT/US2012/030121
§ 371 (c)(1),
(2), (4) Date: Feb. 3, 2014

(87) PCT Pub. No.: WO2012/129404
PCT Pub. Date: Sep. 27, 2012

(65) Prior Publication Data
US 2014/0139847 A1    May 22, 2014

Related U.S. Application Data

(60) Provisional application No. 61/466,142, filed on Mar. 22, 2011.

(51) Int. Cl.
*G01N 21/43* (2006.01)
*G01N 21/45* (2006.01)
*G01N 21/49* (2006.01)
*G01N 21/84* (2006.01)

(52) U.S. Cl.
CPC ............... *G01N 21/45* (2013.01); *G01N 21/49* (2013.01); *G01N 21/84* (2013.01)

(58) Field of Classification Search
CPC ........... G01B 9/02027; G01B 9/02029; G01B 9/02083; G01B 9/02087; G01B 9/02079; G01B 9/02081

USPC .................................................. 356/481, 517
See application file for complete search history.

(56) References Cited

U.S. PATENT DOCUMENTS

| | | | | |
|---|---|---|---|---|
| 2004/0100637 A1* | 5/2004 | Teich et al. | .................... | 356/497 |
| 2009/0194702 A1 | 8/2009 | Meyers et al. | | |
| 2010/0027021 A1 | 2/2010 | Nebosis et al. | | |

FOREIGN PATENT DOCUMENTS

| | | |
|---|---|---|
| EP | 2293031 A2 | 9/2011 |
| WO | 2010/129027 A2 | 11/2010 |

OTHER PUBLICATIONS

International Search Report and Written Opinion under date of mailing of May 23, 2012 in connection with PCT/US2012/030121.

* cited by examiner

*Primary Examiner* — Jonathan Hansen
(74) *Attorney, Agent, or Firm* — Yakov Sidorin; Quarles & Brady LLP

(57) ABSTRACT

An optical system and method for characterizing an object is provided. The system includes at least one light source configured to direct photons toward an object and an interferometer configured to receive photons from the object. The system also includes at least one detector system adapted to detect an optical signal at an output of the interferometer and to remove, from the detected optical signal, a signal portion representing first order photon correlations, when present. The system also includes a processor configured to receive data relating to second-order correlated photons from said at least one detector system, each photon or photon pair subject to at least two indistinguishable paths to a photon or photon pair, but differing in at least one of time and length. The processor is configured to characterize the object based on a self interference of the second-order correlated photons from a common location within the object.

31 Claims, 9 Drawing Sheets

DETERMINATION OF A MATERIAL CHARACTERISTIC WITH THE USE OF SECOND-ORDER PHOTON CORRELATION

CROSS-REFERENCE TO RELATED APPLICATIONS

This application represents the national stage entry of PCT International Application No. PCT/US2012/030121 filed on Mar. 22, 2012, and claims the benefit of U.S. Provisional Application Ser. No. 61/466,142, filed Mar. 22, 2011. The disclosure of each of these applications is incorporated by reference for all purposes as if set forth in their entirety herein.

TECHNICAL FIELD

The present invention relates to determination, via optical imaging, of whether a sample includes lipid material and, more particularly, to such determination made by forming an image of thermally-generated second-order photon correlations in an interferometric system that is operable as an optical coherence system.

BACKGROUND ART

Myocardial infarction (MI) is extremely common worldwide. It occurs following the rupture of small, usually thin-walled lipid-filled plaques in the coronary arteries. When such plaques rupture, they release thrombogenic factors into the blood, causing a cascading sequence of events that culminates with clot formation and blood vessel occlusion. The plaques that obstruct a relatively small percentage of the lumen (for example, about 15% or so) have been undetectable by conventional imaging modalities (due to, primarily, insufficient resolution). The commercialization of the OCT systems and methods alleviated this situation to some degree. However, although the optical coherence tomography (OCT) imaging modality was shown to identify small plaques and their thin intimate, thin-walled caps (about 75 microns in diameter or less), when used for intravascular imaging, it is well recognized that the ability of the OCT to distinguish lipid plaque material (which is intravascularly unstable) from non-lipid plaque material (which has higher stability) is quite poor. Indeed, both the lipid and non-lipid appear similar (for example, dark) when imaged with an OCT system. As a result, interventional treatments cannot be performed on the otherwise visible thin-capped intravascular plaques until the lipid nature of these plaques if identified reliably.

Overcoming this obstacle is essential for therapeutic treatment related to plaques that cause most of the MIs. It has been proposed that in an OCT-image of a plaque, a diffuse (non-sharp) border between the intima and the core of the plaque may be indicative of the presence of lipid material. However, our prior work shows that such diffuse boundary could be explained by surface scattering in the intima of the plaque. (See, for example, Brezinski M. E. et al, Assessing atherosclerotic plaque morphology: Comparison of optical coherence tomography and high frequency intravascular ultrasound. *Heart.* 77:397-403, 1997, PMID: 9196405). FIG. 7 is a pictorial representation of an OCT image of a plaque, where the diffuse cap-lipid interface (traced with a dashed line 710 and pointed out with an arrow 712) is covered with a highly-scattering cap (seen in the upper "reflectogram" portion of FIG. 7 as an area 716 producing significant reflections). Arrows 718 identify a cap with lower scattering and the cap-lipid interface in this area is sharply defined. Arrows 720 indicate the intima-elastic layer interface (no lipid preset) that is diffuse, with an intima that is highly scattering. The above-mentioned surface-scattering explanation of the diffuse boundary appearing in the OCT images was confirmed by independent studies that showed the identification of lipid plaques based on the diffuse border in an image with insufficient sensitivity and/or reliability of 83% and as low as 43%, for example.

There remains a persisting need, therefore, in developing a technique that would allow the reliable and repeatable lipid-plaque identification and the ability to unambiguously distinguish a lipid plaque from a non-lipid plaque. Embodiments of the present invention address such need by employing aspects of the OCT-based approach that have been previously neglected in related art.

SUMMARY OF THE INVENTION

Embodiments of the invention provide a device for characterizing an object. The system may include at least one light source configured to direct photons toward an object and an interferometer configured to receive photons from the object. The system also includes at least one detector system adapted to detect an optical signal at an output of the interferometer and to remove, from the detected optical signal, a signal portion representing first order photon correlations, when present. The system also includes a processor configured to receive data relating to second-order correlated photons from said at least one detector system, each photon or photon pair subject to at least two indistinguishable paths to a photon or photon pair, but differing in at least one of time and length. The processor is configured to characterize the object based on a self interference of the second-order correlated photons from a common location within the object.

The device may also include at least one light source configured to direct photons toward an object (for example, a non-quantum source of light) and an interferometer configured to receive photons from the object. The photons can be directed toward the object through an optically-misbalanced interferometer nested in an arm of said interferometer. The device further includes at least one detector system adapted to detect an optical signal at an output of the interferometer and to remove, from the detected optical signal, a signal portion representing first order photon correlations, when present. In one embodiment, the removal of the signal portion representing first order photon correlations causes the output of the one or more detector system contain only data related to second-order correlated photons. The device further includes a processor configured to receive data relating to second-order correlated photons from the above-mentioned detector system, each photon (or, alternatively, a photon pair) subject to at least two paths that are indistinguishable but differing in at least one of time and length. The processor is further configured to characterize the object based on a self interference of the second-order correlated photons from a common location within the object.

Optionally, the processor is additionally configured to generate a profile of second-order correlations (SOC) of light the common location within the object, the profile being indicative of a material characteristic of the object. The above-mentioned detector system includes at least one of (i) an optical detection system operable in a single-channel detection mode and a dual-channel balanced detection mode and (ii) multiple optical detectors. The interferometer include, in its arm, one or more of a component configured to vary optical dispersion, a varying optical delay line, a varying time delay line, a diffraction grating, a second optically-misbalanced interferometer, an element configured to vary polarization of light, a birefringent medium, and an element producing a double reflection of light.

Embodiments of the present invention also provide a method for determining a material characteristic of an object with the use of an optical system that includes a first interferometer having an input and an output and a second interferometer in an arm of the first interferometer. The imaging system further includes an optical detector system operable in and switchable between a single-channel and dual-channel balanced detector modes. Such detector system is configured in optical communication with the output. The method includes (i) illuminating the object with incident light through the sample arm; (ii) receiving, with the detector system switched to operate in the single-channel detector mode, incident light form the second interferometer that has reflected off from the object to acquire first data associated with an optical scan of the object; and (iii) receiving, with the detector system switched to operate in the dual-channel detector mode, incident light from the second interferometer that has reflected off from the object to form acquired second data associated with an optical scan of the object. The method also optionally includes imaging the object to identify a reflective interface at the object.

In addition, a method includes processing, in a computer process, the first and second data to derive second-order correlations data representing a material characteristic of the object. In a specific implementation, such processing of data includes subtracting the second data from the first data. The method optionally further includes plotting so derived second-order correlations data as a function of a position inside the object to form a plot representative of the material characteristic of the object, for example a type of material of the object. In a specific case, the material characteristic of the object includes lipid in the object. In a specific case, the object includes an intravascular plaque.

The light detected with the optical detection system includes light from the reference arm of said first interferometer and, in one embodiment, includes light subject to an optical delay line operable to modify optical dispersion in the reference arm of the first interferometer. The operation of the optical delay line, resulting in the change of the optical dispersion, causes a chirp in light distribution with which at least one of the first and second data are associated.

The method optionally includes, in addition, changing optical dispersion in an arm of the first interferometer which, in a specific embodiment, includes changing optical dispersion in a variable optical delay line of an arm of the first interferometer. Alternatively or in addition, the method includes receiving, with an optical detection system, light that has reflected off from the object and that has traversed only one arm of the second interferometer upon propagation towards the output of the first interferometer, to acquire a third set of interferometric data.

BRIEF DESCRIPTION OF THE DRAWINGS

The invention will be more fully understood by referring to the following Detailed Description in conjunction with the Drawings, of which:

FIG. 3A is a plot illustrating chirp frequencies in an interferogram formed with an embodiment of the optical imaging and detected by an optical detection system operated in a single-channel detector mode.

DETAILED DESCRIPTION

Figure 1:
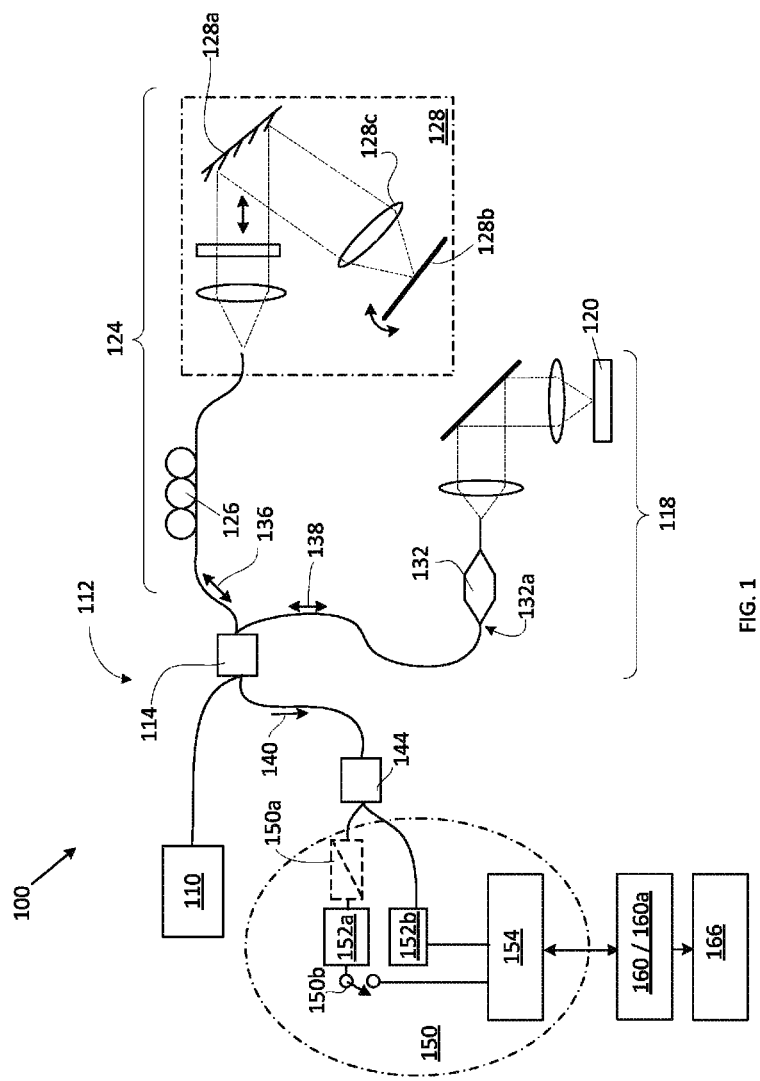
FIG. 1 is an embodiment of the optical imaging system of the present invention.

As will be appreciated by one of ordinary skill in the art, the following description of the invention, at least at times, describes the systems and methods with a deference to classical physics, though such description may obviously be at odds with a description more fundamental to quantum mechanics. However, as will also be appreciated by one of ordinary skill in the art, the operations of the following systems and methods can be more clearly understood with deference toward a description based on quantum mechanics. As such, the description also includes describes the systems and methods with reference to quantum mechanics. Thus, at times there are variations in concepts between classical physics and quantum mechanics. However, these variations will be understood by one of ordinary skill in the art.

According to embodiments of the invention, imaging methods and apparatus are disclosed that employ a thermal optical source to acquire, in light reflected by an object or sample through indistinguishable optical paths and the use of a detector system adapted to detect an optical signal at an output of the interferometer and to remove, from the detected optical signal, a signal portion representing first order photon correlations, when present. Optionally, such detector system is adapted for complementary use of single and dual balanced detection in the same interferometric system. Based on this second-order correlations data, a quantum mechanical analysis of superposition of media at the interface of the object or sample is conducted. For example, a processor of the apparatus is configured to receive data relating to second-order correlated photons from the above-mentioned detector system, each photon or photon pair being subject to at least two paths that are indistinguishable to the photon or photon pair but differing in at least one of time and length. In particular, a system and method of the invention assess local material composition at an interface of first and second media having different refractive indices. An assessment is made of differences in refractive indices of samples interrogated with such system, thereby enabling distinction of two media having different material compositions. The second-order correlations in low-coherence interferometric (LCI) system, that cause nonlocal quantum entanglement, are employed independently from the first-order correlations to provide diagnostic information about interrogated samples by measuring sample parameters such as refractive index and local decoherence rates.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

In a conventional implementation of the LCI modality (for example, an optical coherence tomography, OCT, arrangement), light such as the IR light from the low coherence optical source is coupled into an scanning interferometer (for example, a Michelson interferometer) that has a sample in its sample arm, and first order correlation interferometric data (produced by unpaired photons) is utilized to determine the intensity distribution of the detected interferogram as a function of depth in the sample with the spatial resolution on the order of a few microns (for example, about 2 to about 4 microns). The LCI provides an example of first order correlations, resulting from interference of a single photon with itself.

Photon correlations of second order, referred to as bunched photons (or inseparable photon wavepackets, or indistinguishable photons), result from interference of photon pairs with themselves. The second-order photon correlations represent a significant percentage of photons emitted by the LCI/OCT sources. The second order correlations correspond to a single entity (characterized, for example, by nonfactorizable multiparticle state and indistinguishable optical paths), and can be separable (classical), entangled (quantum), and non-separable correlated, and are distinct from classical first-order correlations conventionally used for imaging in LCI based imaging systems. Despite recent indications that determination of the quantum properties of paired photons (and, in particular, what is known as second order correlations or SOC) can be useful for assessing material media, conventional OCT imaging systems and methods for processing of imaging data acquired with such systems routinely subtract or negate the SOC data from the OCT interferograms and interferometrically-acquired data as unwanted noise and, as a result, do not take into account entanglement of macroscopic objects at the ends of the arms of an interferometer. (See, for example, a discussion by M. E. Brezinski et al. in *Phys. Rev. A*, 78, 0639824, 2008.)

Implementations of the present invention stem from the realization that the use of traditionally discarded, by related art, quantum phenomena and SOC data acquired with an LCI or OCT-like interferometric imaging system allows to distinguish differences in material properties of dissimilar samples interrogated with such OCT imaging system. In particular, distinguishing between lipid-containing and lipid-free samples is effectuated by analyzing changes in SOC data obtained in reflection of such samples. It is noted that, in some configurations or clinical settings a "lipid-free" sample or object or a "lack of lipid" may be desirably indicated with a percentage of lipid is actually present in the sample or object, such as when the percentage of lipid is less than 20 percent. More specifically, distinguishing the intravascular lipid plaques from non-lipid plaques employs a SOC measurement based on the measurement of refractive index (RI) differences between the lipid-based and non-lipid-based elements of a plaque.

Measurement of the SOC can be viewed as the measurement of photon pairs with two detectors in a given time interval. Photons and photo pairs interfere presented with quantum-mechanically indistinguishable paths. Quantum SOC phenomena are observed with the use of various optical sources, for instance, including a swept source configured to sweep across a predetermined bandwidth, a non-entangled source, a thermal optical source, multiple source, and the like. It is noted that with some sources, for example, a swept source, the interferometer does not use a moving mirror in the delay line and the Fourier transform (or similar) is obtained from the frequency swept information (either single or dual). Also, the source may be a fixed broad band source and also be associated with a fixed reference arm delay relative to sample arm.

Three primary types of photons lead to SOC: entangled (inseparable) photons, thermal (partially separable) photons, and separable (coherent) photons. Unlike the first-order correlations, the quantum effects produced by entangled and/or thermal photons have practical implications on a microscopic scale. Using the first and second order coherence functions, $G_1$ and $G_2$, the SOC corresponding to these types of photons are expressed as for separable photons $$G^{(2)}(r_1,t_1;r_2,t_2) = G_{11}^{(1)} G_{22}^{(1)} \text{ for separable photons}$$

$$G^{(2)}(r_1,t_1;r_2,t_2) = G_{11}^{(1)} G_{22}^{(1)} |G_{12}^{(1)}|^2 \text{ for thermal photons}$$

$$G^{(2)}(r_1,t_1;r_2,t_2) = |\Psi(r_1,t_1;r_2,t_2)|^2 \text{ for entangled photons} \quad (1)$$

For coherent light, the SOC function is the product of the two first order correlation functions, events registered at the two detectors are separable, and no quantum effects occur. In the entangled situation, the two photons are in one entangled state until such state is perturbed. The corresponding SOC function includes a phase factor and the corresponding interferometric amplitude can range from negative to positive. The SOC corresponding to thermal radiation includes both the product of corresponding (separable) first order correlations for two interferometric arms and a quantum mechanical term $G_{12}$ related to correlation and anticorrelation and representing phase differences between the indistinguishable paths in the used interferometric system. The use of thermal optical sources allows, therefore, to gain an insight into an interrogated sample from the quantum mechanical portion of the SOC while avoiding the limitations associated with quantum sources (such as inadequate number of photons, for example). Another advantage of using thermal optical sources, according to embodiments of the invention, is an OCT imaging procedure can accompany the SOC assessment and be carried out contemporaneously with such SOC assessment.

FIG. 1 is a diagram illustrating an embodiment 100 of an interferometric imaging system including a time-domain LCI apparatus with dual channel balanced detection. The embodiment 100 employs a thermal source of light 110 (as shown, a superluminescent diode SLD generating about 10 mW of light output at about 1310 nm, with signal to noise ratio, SNR, of about 102 dB; by AFC, Canada). More generally, the optical source 110 includes generally a non-quantum optical source generating non-entangled photons (such as a pseudo-thermal optical source or a thermal optical source). Light output from the source 110 is delivered towards an interferometer 112. Light further passes through a first beam-splitter 114 (such as a partial mirror or a fiber-optic coupler, as shown) towards a sample arm 118, containing a sample 120 and appropriate auxiliary optical components such as a lenses and reflectors. Light from the source 110 is also passed on to a reference arm 124 of the interferometer 112, which includes an optional polarization controller 126 (such as a fiber-optic based variable linear polarizer, for example, as shown) and an optional delay line 128. The optional delay line 128 contains a diffraction grating 128a and a (polarization sensitive) mirror 128b the orientation and/or position of which can be adjusted by, for example, displacing or rotating the mirror such as to change an angle of inclination between the grating 128a and the mirror 128b. Among the auxiliary optical components of the reference arm 124 there is a lens 128c positioned between the grating 128a and the mirror 128b to focus incident light onto a surface of the mirror 128b. In an embodiment where the optional delay line 128 is absent (not shown in FIG. 1), the reference arm 124 may terminate with a reflector, for example.

Light from the sample arm 118 passes through an optically mismatched interferometer 132 (as shown, a fiber-optic based Mach-Zehnder interferometer configured to have arms with optical path difference that is adjustable, for example, via appropriately arranged optical couplers) that is part of the arm 118. As shown, the interferometer 132 is internal to and nested in the interferometer 112. Therefore, the interferometer 112 is referred to as the outer interferometer. Upon passing through the nested, inner interferometer 132 (and in combination with light 136, shown with an arrow, from the reference arm 124 of the outer interferometer 112), light 138 from the sample arm 118 forms an interferometric distribution of light 140. Light 140 contains SOC information associated with the sample 120.

It is appreciated that the inner interferometer 132 is generally configured to deliver two portions of light, reflected off from the sample 120, to a junction 132a. The first portion of light from one arm of the inner interferometer 132 while the second portion of light from another arm of the same interferometer. Due to the fact that the inner interferometer is optically misbalanced (i.e., its arms have different optical lengths), one of the first and second portions of light arrive at the junction 132a later than another portion. Accordingly, the inner interferometer 132 can be optionally substituted by an optical element that is placed in an arm of the outer interferometer 112 and that is configured to transmit first light from the input of the outer interferometer 112 to an end of such arm and to define (in transmission from the end of this arm towards the output of the outer interferometer 112) two portions of light one of which is time-delayed with respect to another. An example of such optical element is provided by a reflector forming two reflections (for example, reflections from different reflecting surfaces).

The embodiment 100 also includes an optional means (not shown) of blocking a beam in one of the arms of the mismatched interferometer 132. In an embodiment where there is a sub-interferometer or with a double reflector, if one arm is closed or otherwise made into a single reflection, LCI or OCT data can be collected. It is noted that, generally speaking, OCT is LCI scanned in two or three dimensions. With respect to the double reflector, if the top layer is linearly polarized, for example, and there is a linear polarization filter in the arm, when both arm aligned, a double reflection is achieved. When they are perpendicular, only a reflection off the top layer is achieved so the system is in the LCI or OCT mode.

Light corresponding to the interferogram 140 is further split and by a second beam-splitter 144 (as shown, a fiber-optic 50:50 coupler) and delivered to an optical detection system 150 that is configured to be switchable between a single-channel detection system that employs a detector 152a and a dual-channel balanced detection (DBD) system that employs detectors 152a, 152b. The switching or reconfiguration of the detection system 150 between the single-channel and dual-channel detection modes is accomplished, for example, with the use of an optical switch 150a or with the use of an electronic switch 150b (both of which are shown in FIG. 1, although the simultaneous use of both switches is not required). For example, when the optical detection system 150 is configured to operate in a DBD mode, the second beam-splitter 144 redirects light of the interferogram 140 as two portions of light (respectively corresponding to two interferograms that are 180 degrees out of phase but otherwise are identical) to the detectors 152a, 152b of the detection system 150. Optical data acquired with the detection system 150 is further relayed to electronic circuitry 154 of the optical detections system 150, as well as a data processor 160 and an associated tangible, non-transitory, computer-readable storage medium 160a embodying computer program code governing the operation of the processor 160 (and, optionally, other devices of the embodiment 100). The storage medium 160a is additionally adapted for storage of data.

Figure 2A:
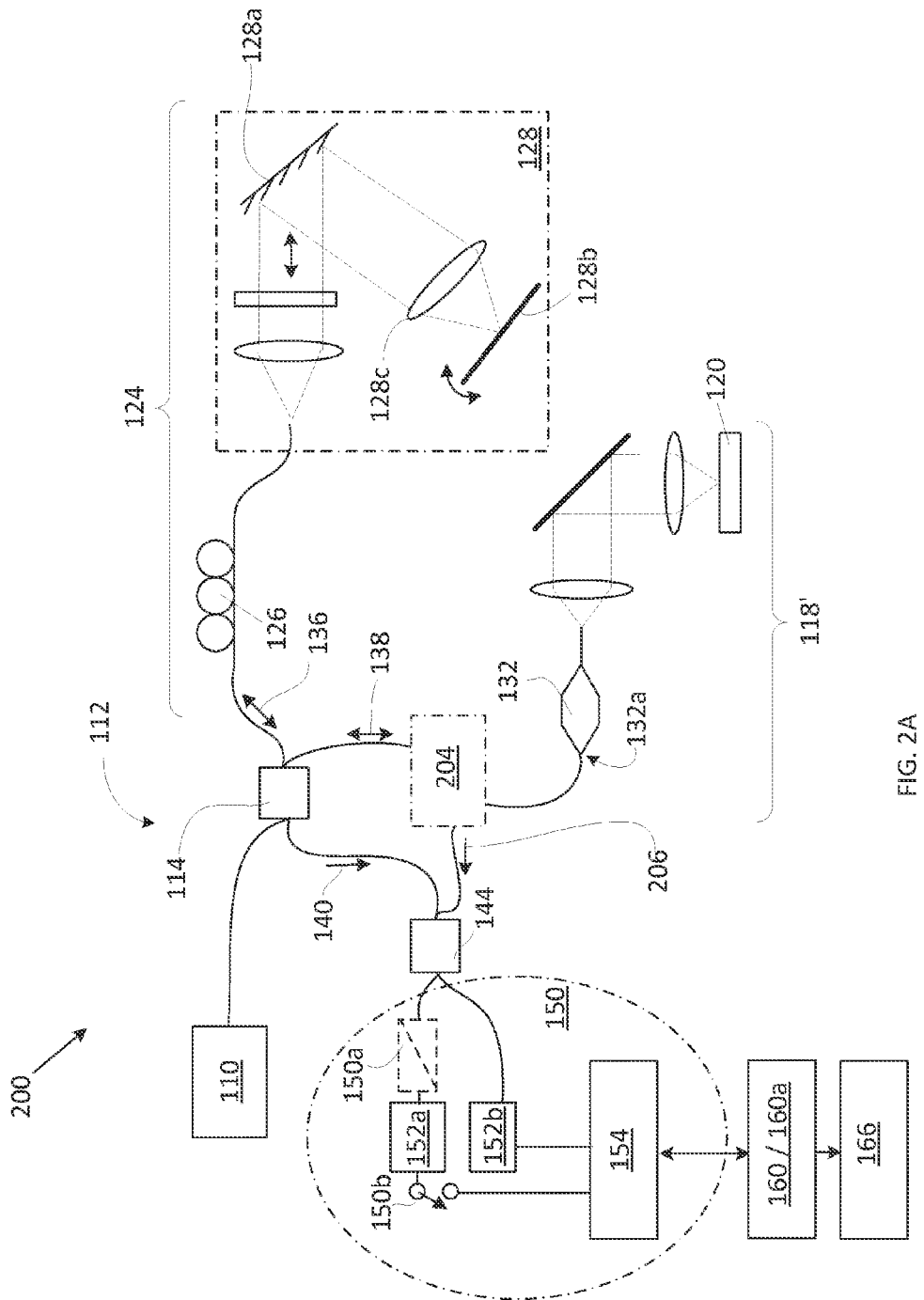
FIG. 2A is an alternative embodiment of the optical imaging system of the present invention.
Figure 2B:
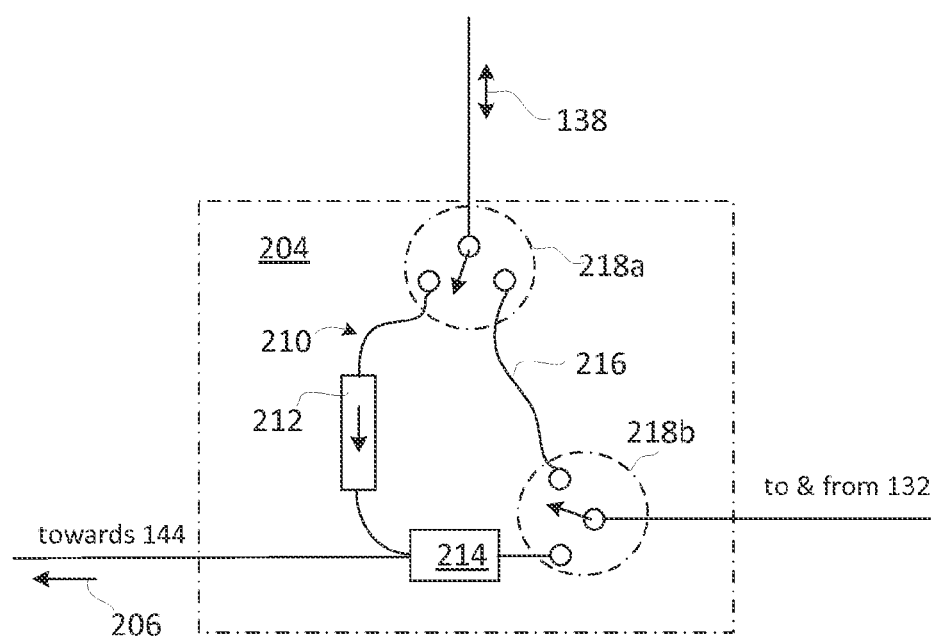
FIG. 2B is a diagram illustrating an optical router of the embodiment of FIG. 2A.

A related embodiment 200 is illustrated in diagrams of FIGS. 2A and 2B in which, in comparison with the embodiment 100 of FIG. 1, the sample arm 118' additionally contains an optical router 204 configured to be in optical communication with the beam-splitter 114, the inner interferometer 132, and with a beam-splitter 144 (via an optical path 206). The optical router 204 includes optical by-pass branches: an optical isolator branch 210 with an optical isolator 212 and a coupler/beamsplitter 214 and a branch 216. The optical switching between the branches 210, 216 is effectuated with switches 218a, 218b that enable switching of the operation of the embodiment 200 between a first mode, in which the embodiment 200 operates as an OCT imaging system, and a second mode in which the SOC interferometric signal is registerable by the optical detection system 150. The embodiment 200 is advantageous in that an optical signal detected by the detection system 150 in either the first or second mode has the same irradiance and, therefore, no dynamic gain of the detected signal is required. At least one of the switches 218a, 218b is optionally configured as an optical switch as known in the art. The router 204 is configured to optimize and/or even and/or compensate the difference between optical paths for the single-channel and dual-channel detection sub-systems of the system 150.

Figure 2C:
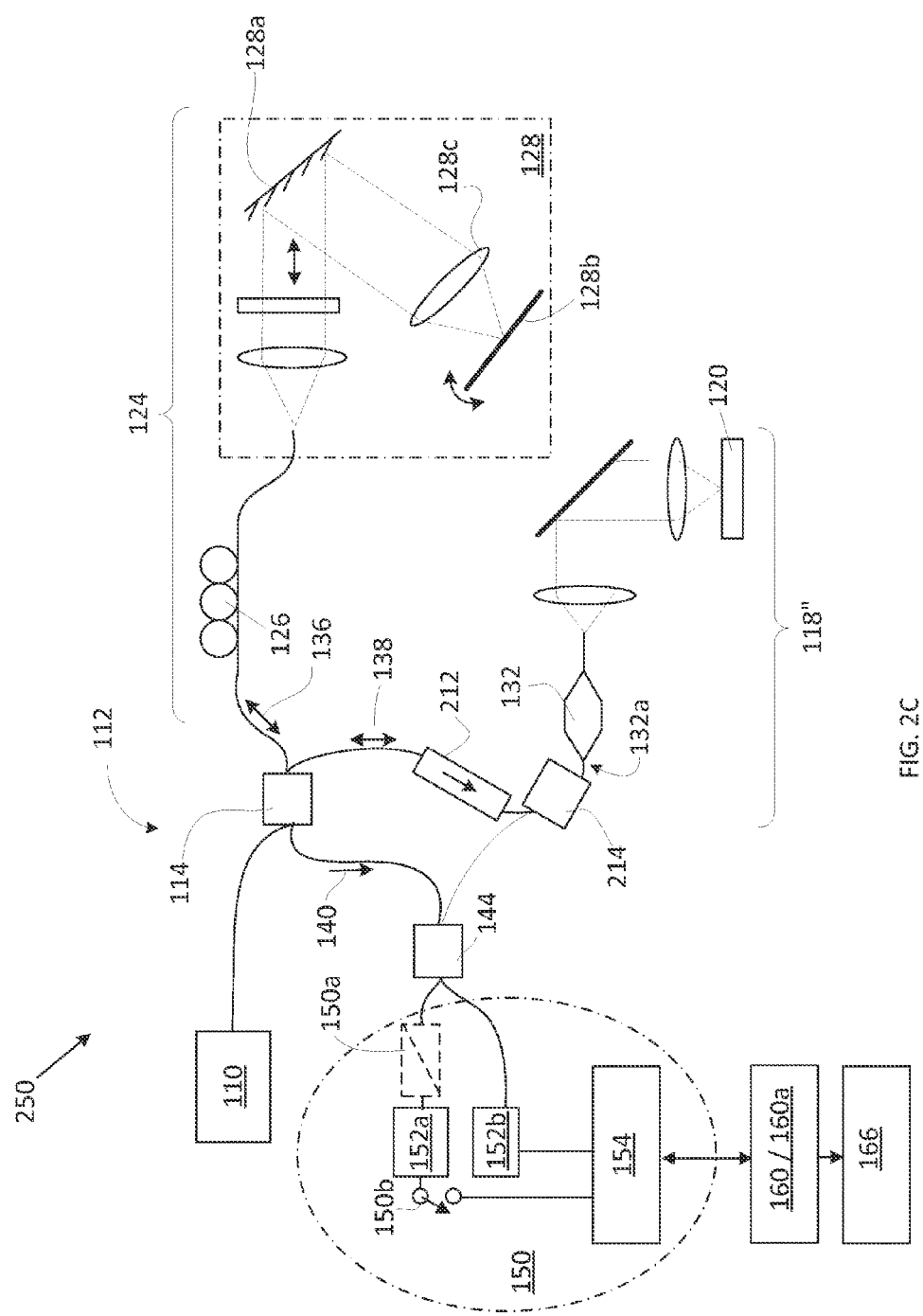
FIG. 2C is a diagram illustrating an alternative embodiment of the invention.

Yet another related embodiment 250 is shown schematically in FIG. 2C. Here, a dual-channel interferometric setup is shown, wherein the isolator 212 and the coupler 214 are used in operation with a DBD mode (and not used when the detection system operated in a single-channel detection mode).

The sample 120 may include two spatially-separated reflective surfaces (a double reflector). In one implementation, for example, the sample 120 may incorporate two optically-thick (~1 mm or thicker) glass slides a gap (about 10 to 50 micron wide) between which is filed with a chosen medium such as lipid material and non-lipid material (for example, water or air). However, due to the fact that processing of optical data in embodiments of the invention is performed in time domain rather than in spatial domain, embodiments of the invention make the presence of a single reflective surface in a sample sufficient for determination of the SOC data. Accordingly, in a related embodiment the sample 120 includes a single reflecting surface at which a material mixture is disposed. In one example, a mixture of lipids and water can be disposed at a surface of optically-thick glass slide that, considering the difference of refractive indices in the material mixture and the glass, partially reflects light delivered to such sample from the thermal (or, generally, pseudo-thermal) source 110. In different measurements the ratio of lipids to water content in the mixture is optionally varied, for example in 10% steps between 0% and 100%. In another example, where the interrogated sample includes an intravascular plaque, the reflective surface may include a cap of the plaque.

In continuing reference to FIGS. 1, 2A, and 2C, the operation of the optional delay line 128 (and, in particular, the displacement of the mirror 128b) causes a change in optical dispersion in an arm of the interferometer 112, thereby defining a varying chirp in the interferogram 140. (According to implementations of the invention, however, there is no requirement that dispersion be varied only in the reference arm 124, and such variation can be alternatively implemented in the sample arm 118.) Such change in optical dispersion effectively amounts to an uncertainty of positions of the reflecting elements of the sample 120 (i.e., for example, the uncertainty of positions of the reflecting surface and the material mixture) in the sample arm 118, induced through entanglement of the SOC. It is noted that the spatial spread of the uncertain positions of the reflecting elements of the sample 120 (sample arm 118) is a purely quantum mechanical phenomenon induced by non-local events (reference arm 124), resulting in macroscopic superposition or overlap of the locations of the reflecting elements of the sample 120 as viewed in light detected with the detection system 150. The quantum nature of this effect is confirmed by varying the contents of the mixture, which does not affect classical dispersion but does affect the position probability amplitude.

It is appreciated that if the grating 128a is placed at a location other than a location of the focal point on a lens 128c of the delay line 128, the equivalent group velocity dispersion (GVD) value induced in the reference arm 124 is invariant with respect to the distance of separation between the grating 128a and the lens 128c.

The first set of interferometric data acquired with an imaging system (such as that on one of the embodiments 100, 200) when only a signal-channel of the detection system 150 is engaged includes data representing both the first and second order photon correlations. As the mirror 128b is displaced, the width of each peak in the detected interferogram is being changed (for example, increased) until the chirping occurs. The spatial frequency(ies) characterizing this chirping is determined by performing a Fourier transform of the data acquired for each scan with the use of the processor 160 and optionally plotted as a function of mirror displacement (for example, presented for visualization and/or analysis on a display device 166). Similarly, the second set of interferometric data is then acquired with the imaging system now switched to a double-channel balanced detection system (that is adapted to measure the first-order correlations in detected signal). The second set of interferometric data contains predominantly the data related to the first order correlation of photons. Accordingly, the acquisition of both data sets with the switchable detection system 150 enables the determination of data representing solely the SOC of paired photons in the interferometric system 100 by appropriately combining the first and second sets of data, in particular, by subtraction of the second set of data from the firs set of data.

Figure 3A:
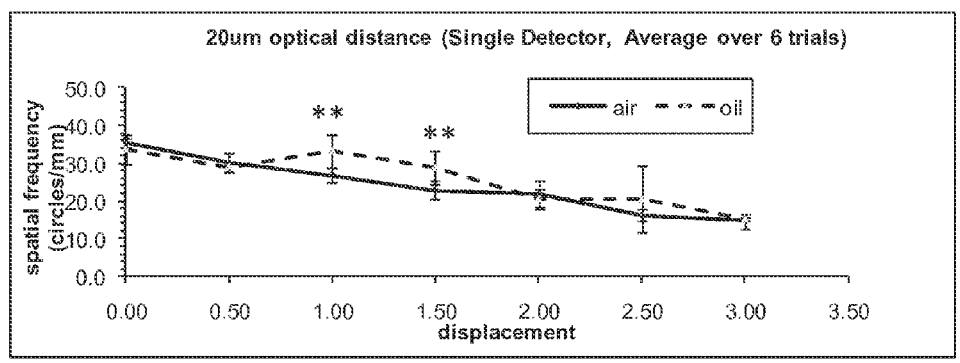
FIG. 3A is a diagram illustrating an alternative embodiment of the imaging system.
Figure 3B:
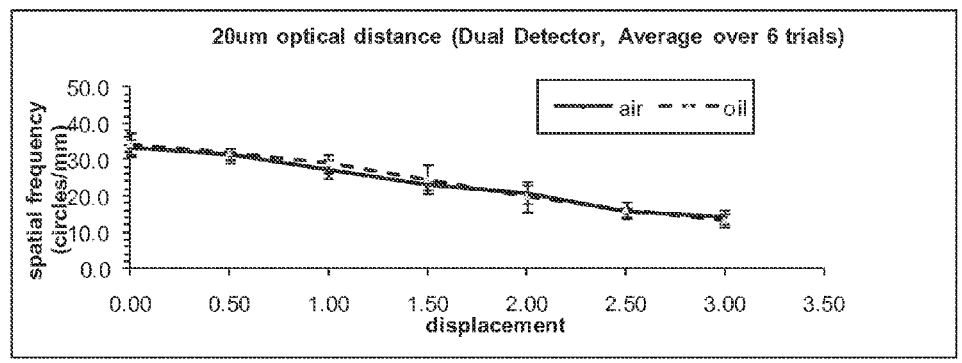
FIG. 3B is a plot illustrating chirp frequencies in an interferogram formed with an embodiment of the optical imaging and detected by an optical detection system operated in a single-channel detector mode.

As FIGS. 3A and 3B illustrate, statistically significant differences exist between spatial (chirp) frequencies that were determined from the interferogram 140 of FIG. 1 acquired with a single-channel detector subsystem of an embodiment for two samples containing lipid and air, respectively. (The notations "**" used in FIG. 3A represent $p<0.01$ or lower.) In contradistinction, when the resulting interferogram 140 is detected with a DBD subsystem, no statistically-significant difference among the samples was observed (see FIG. 3B). Similar results were obtained from the comparison between the measurements of samples containing water and air, respectively. Such differences in experimental data are not explained in a classical model, but are accounted for when considering the SOC (the $G_{12}$ term of Eq. 1) of a photon from the thermal source interfering through indistinguishable optical paths, as discussed further below. Indeed, frequency chirping in a classical (non quantum mechanical) model should not depend on the medium of the sample at a constant optical distance and be a function of the presence or absence of the SOC.

Figure 4A:
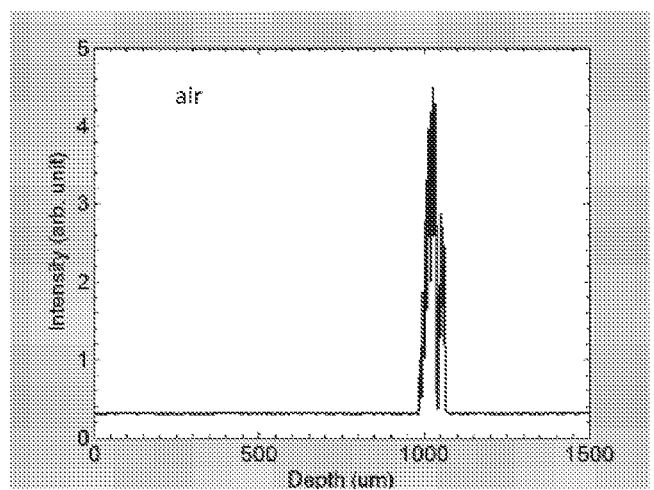
FIGS. 4A, 4B, and 4C are plots of intensity of light versus sample/object depth (for samples including air on the reflective surface, water on the reflective surface, and oil on the reflective surface, respectively) as acquired with an embodiment of the optical imaging system configured to operate as an OCT imaging system.
Figure 4B:
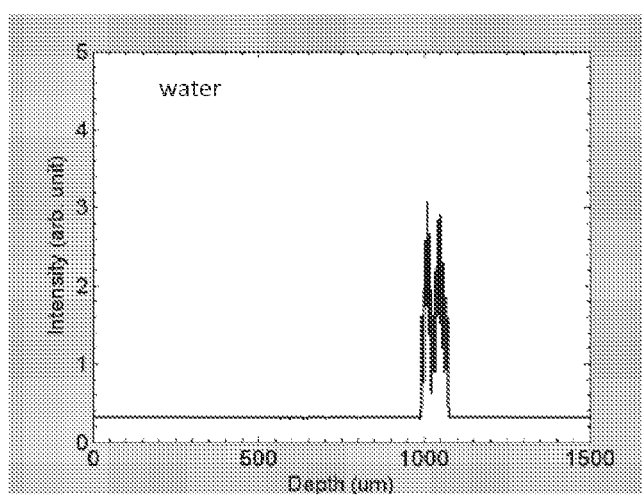
Figure 4C:
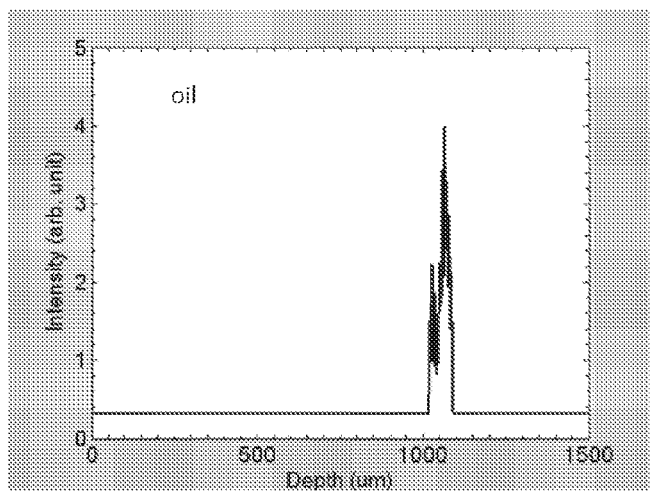
Figure 5A:
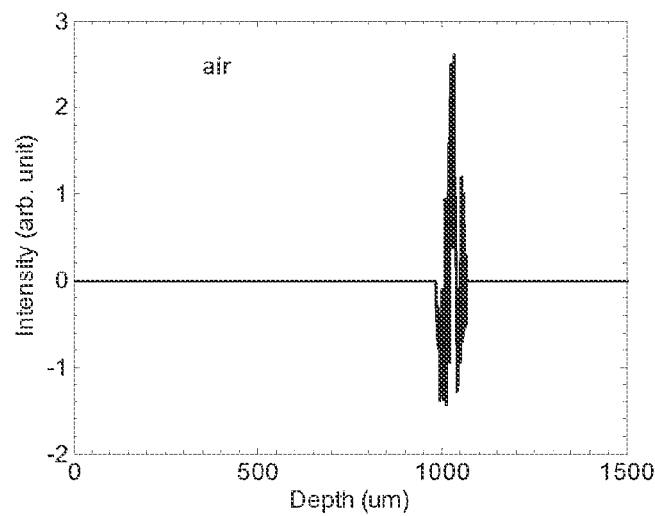
FIGS. 5A, 5B, and 5C are plots of intensity data corresponding to second-order correlations acquired with an embodiment of the optical imaging system from samples/objects including, respectively, air on the reflective surface, water on the reflective surface, and oil on the reflective surface.
Figure 5B:
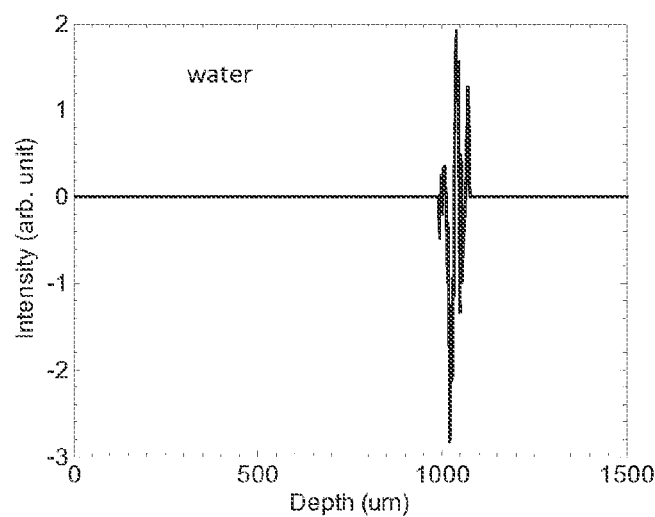
Figure 5C:
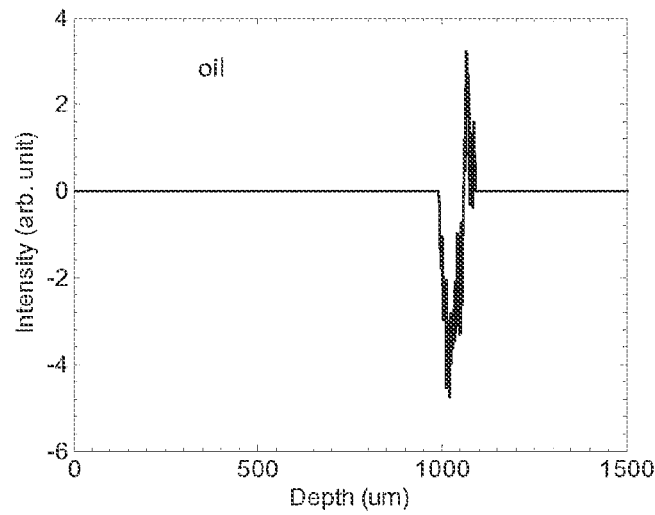

FIGS. 4A, 4B, and 4C are plots of intensity versus sample depth obtained from the conventional LCI-configured dual-channel detector measurements of different samples that contain respectively air, water, and lipid (oil) on a surface of a glass slide. These optical scan measurements were carried out with an embodiment of the interferometric imaging system switched into operation under the conditions of zero dispersion and a 40 micron optical path difference between the arms of the inner interferometer 132. Similar measurements were performed with a single-channel detection scheme to which the same embodiment of the system was reconfigured using the switch 150a/150b. Subtracting the data acquired by the single-channel detection from the results of the dual-channel detection provides respectively-corresponding plots of SOC for the above-mentioned samples in FIGS. 5A, 5B, and 5C. The plots of SOC show graphical features representing a chirp detected in light that has been returned to the optical detection system 150 from the sample 120 through the inner interferometer 132. As shown, these graphical features include peaks of intensity distribution. Such graphically-presented phase information about light that has interrogated the sample 120 is, therefore, indicative of the nature of material nature of the sample 120. In a specific embodiment, where the sample 120 contains, for example, lipid and non-lipid materials, the SOC plots facilitate differentiation of lipid-containing sample from a sample that is devoid of lipid. In particular, and in further reference to FIGS. 5A through 5C, the measurement of the air-glass interface yielded positive SOC, the lipid-glass interface yielded a plot of anti-correlation, and a plot corresponding to the water-glass interface shows biphasic results. The determined SOC results were confirmed to be substantially independent from dispersion introduced by the sample medium, thereby confirming that the SOC represent a change in RI at the interface between the glass and the sample medium. The behavior of the SOC determined with an embodiment of the system of the invention enables, therefore, a discrimination between the lipid and non-lipid samples.

When the interrogated sample includes a single reflecting surface, the SOC peaks produced by an embodiment of the invention include multiple peaks corresponding, generally, to a photon pair interference upon subject to long-and-long, short-and-short, long-and-short, and short-and-long paths of the optically misbalanced inner interferometer (such as, for example, the interferometer 132 of FIG. 1). At least four potential paths exist for photons subject to the inner interferometer 132 and to generate the interferogram at the junction 132a. The probability of a specific path to contribute to the interference in the outer interferometer 112 can be generally altered by, for example, the type of a beam-splitter and/or polarization in an arm of the interferometer. (An optional polarization-sensitive element or component and polarization-varying component for use with an arm of the interferometer is discussed further below). Which indistinguishable paths through the inner interferometer 132 contribute to light transmission is, therefore, controllable, and may be optimized for assessment of a given sample. The peaks corresponding to the long-and-long and short-and-short combination is out of phase with the peaks corresponding to short-and-long and long-and-short combination of optical interference paths. In addition, the peaks corresponding to short-and-long and long-and-short optical interference paths are substantially identical. Accordingly, the determination of the SOC correlations can be carried out, generally, by processing the data corresponding to two distinct peaks, two partially overlapping peaks, or a combination thereof.

As understood in light of the above discussion, the analysis of intravascular imaging data acquired with a conventionally-configured OCT system, used by the related art, does not allow, for example, the effective differentiation between lipid and non-lipid plaques. Such differentiation, however, is decisively important in clinical settings. Implementations of the invention employ SOC quantum phenomena neglected by related art to differentiate between lipid and non-lipid plaque, which presents a recognized clinical problem. The SOC are determined in time domain rather than in spatial domain, thereby making it unnecessary to use a sample containing two reflective surfaces. Furthermore, in contradistinction with conventional LCI/OCT imaging systems that remove the SOC-related data as unwanted noise, the present systems and method employ both single- and dual-channel detection capabilities to acquire both the SOC and the conventional LCI/OCT information with the same interferometric system. Instead of distinguishing between lipid and non-lipid based on comparison of chirping frequency as a function of optical dispersion for each of the media of interest (which is impractical in clinical applications), embodiments of the invention relies on identifying negative, positive, or multi-phase peaks to accomplish the same goal.

Referring again to FIGS. 1 and 2A, 2C, embodiments of the invention enable an acquisition of at least three types of imaging data. One type is optical data (first order photon correlation) detected, from a conventional LCI/OCT image with a DBD subsystem of the detection system 150. Another type of data is an optical scan data obtained at, for example, 10 kHz, via interference of light, that has been reflected from the sample 120, at the junction point 132a. Yet another type of data is optical data representing the isolated SOC interferogram obtained by subtracting the optical scan data obtained with a single-channel detection system from that obtained with a DBD sub-system of the detection system 150.

Figure 6:
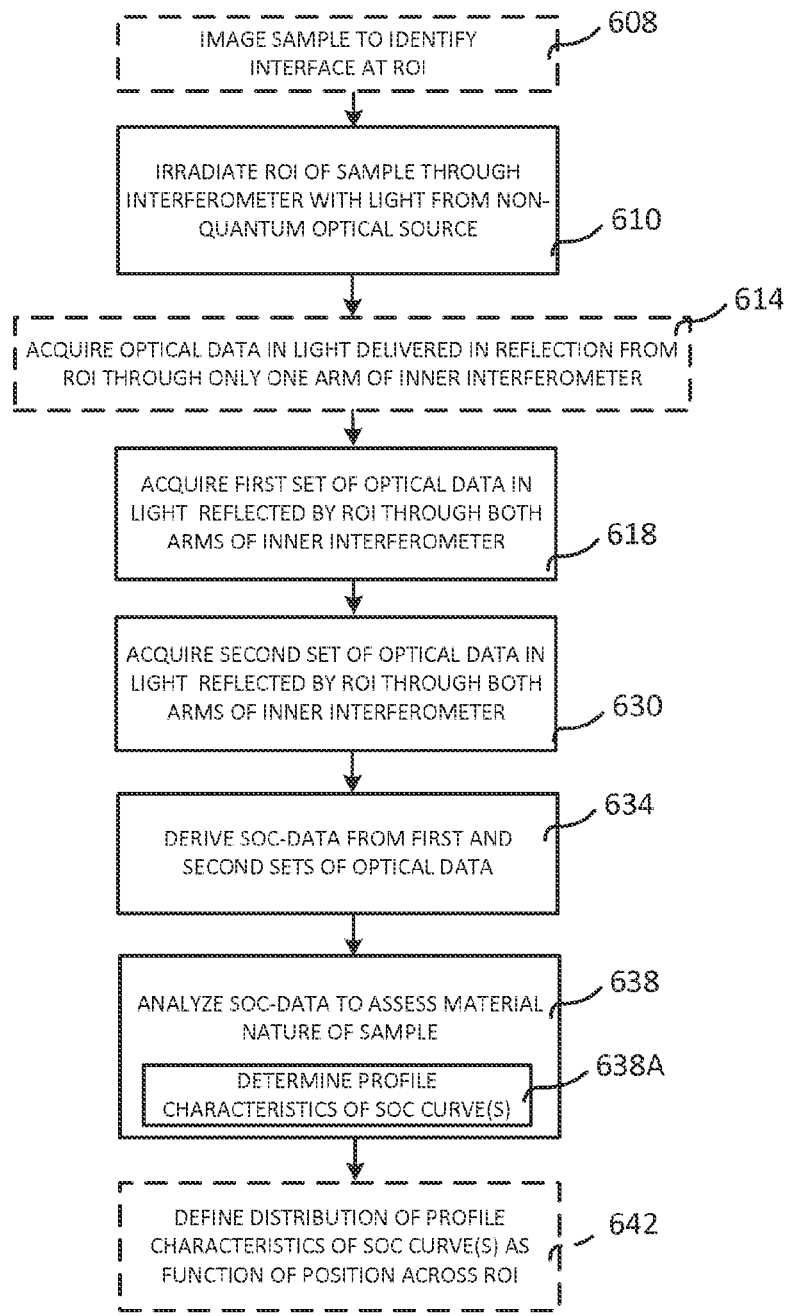
FIG. 6 is a flow-chart illustrating steps of a process in accordance with the present invention, for example, a process of acquiring SOC-data and making a determination of whether lipid is present in the optically-interrogated object is made.
Figure 7:
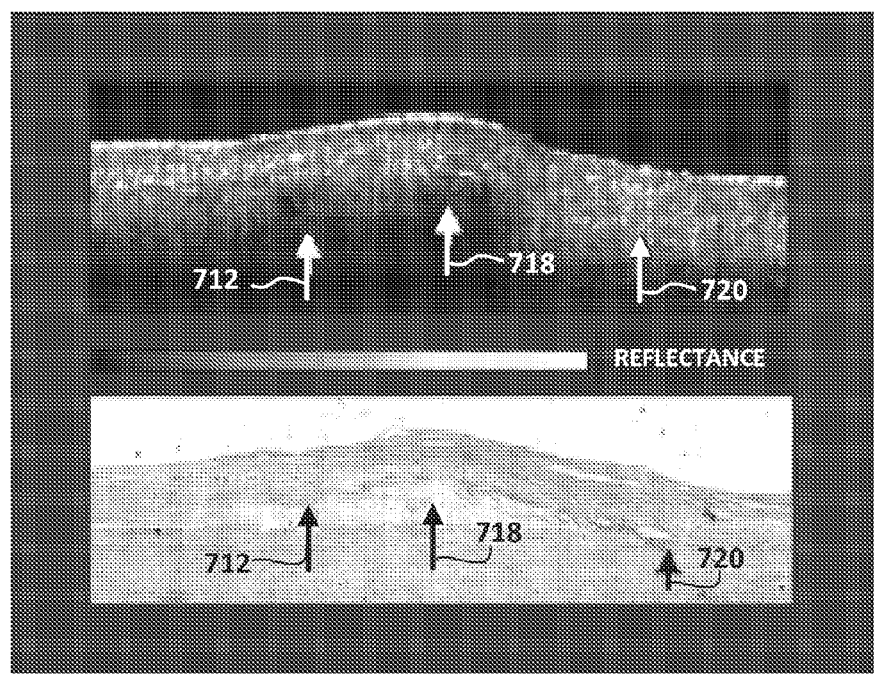
FIG. 7 is two images of an intravascular plaque, including an OCT image, that identify distribution of light scattering off from the elements of the plaque.

Embodiments of the invention are useful and advantageous over systems and methods of the related art in assessing material a material characteristic of the imaged sample. (In a specific case, which is a non-limiting example of possible applications, an embodiment is adapted to differentiate solid plaques such as fibrous/fibrous calcific plaques and lipid-rich plaques in vasculature, for example in arteries. For example, a concentration of lipid in a plaque is measured according to a method of the invention at an interface of the intima and the core using the SOC-signal, detected with an embodiment of the system, and histopathology.) FIG. 6 is a flow-chart illustrating an implementation of a measurement enabling the assessment of the material characteristic of the imaged sample. Optionally, a sample can be imaged, at step 608, to identify a reflecting interface in a region of interest (ROI) of the sample. At step 610, the ROI (for example, vasculature sample containing plaque) is illuminated with light from a non-quantum source of light (for example, a thermal source of light) through the interferometer of the imaging system. At a generally optional step 614, a portion of irradiating light incident onto the sample is retroreflected and delivered, through a sample arm configured not to have split optical paths, to the optical detection system to acquire a set of optical data corresponding to an A-scan the sample, at step 614. For example, when the embodiment 100 of FIG. 1 or the embodiment 200 of FIG. 2A is used, such acquisition is enabled by having one of the arms of the inner interferometer 132 blocked, thereby delivering light reflected by the sample 120 towards the detection system 150 without producing any light overlap at the junction point 132a. At step 614, the ranging of the ROI is performed to confirm the interface identified in sep 608.

Once the reflecting surface of the sample (such as, in a specific example, the intima/core boundary of the illuminated plaque) has been indentified and optionally confirmed, the sample arm of the interferometer of the optical system is reconfigured to accommodate two misbalanced optical paths. This is achieved, for example, by opening a previously blocked arm of the inner interferometer 132 of FIG. 1 or 2A, to configure the sample arm 118 to produce an overlap of time-separated reflections of light off from the sample 120 at the junction point 132a. Consequently, a first set of optical data corresponding to an optical scan of the sample in reflected light (that from the arms of the inner interferometer 132) is collected at the optical detection system at step 618. A second scan of optical data corresponding to an optical scan of the sample in reflected light (that from the arms of the inner interferometer 132) is collected at the optical detection system at step 630. When the first set of optical data is acquired in a single-channel detection mode, the second set of optical data is acquired in a DBD, and vice versa. The switching of the optical detection system between these modes is enabled with the use of switches described in reference to FIGS. 1, 2A, and 2B.)

Data describing the SOC is further derived, at step 634, from the first and second sets of optical data acquired at 618 and 630 by, for example, subtracting one from another. So derived SOC-data is further analyzed at step 638, 638A to determine an indicator of the material characteristic of the sample (such as, in a specific example, the presence of lipid in the plaque). Referring again to FIGS. 5A through 5C, for example, the SOC-data such as intensity of the SOC-signal can be plotted as function of a chosen variable to determine the behavior of the SOC intensity (i.e., the profile of the SOC plots and, particularly, the peaks and troughs and combinations thereof in the plots that serve as material characteristic indicator(s)). In a specific example of a sample containing plaque, plaque regions with substantial amount of lipid are distinguished from plaque regions where less or no lipid is present by comparing the phases of light retroreflected by such regions of the plaque. The phases of light are identified from peaks of the plot, which includes SOC as positive, negative, or mixed peaks.

Values of SOC intensity can be measured as, for example, values averaged over several position across the intima/core boundary of the plaque. In addition, after imaging, a map of the indicator across the ROI can be optionally formed (as shown at step 642). In particular, the changes of the peaks of an SOC curve can be determined by obtaining the results of A-scans at different locations across the reflecting surface of the sample. In one implementation, regions of such map can optionally color-coded to indicate spatial distribution of the material characteristic in the sample. (In a specific example, regions containing little or no lipid can be color coded with trichrome blue while lipid-containing regions can be marked with oil red O. The ratio of intensities of (trichrome/oil red O) marked regions can be further used to asses the 2D map.)

While the invention is described through the above-described exemplary embodiments, it will be understood by those of ordinary skill in the art that modifications to, and variations of, the illustrated embodiments may be made without departing from the inventive concepts disclosed herein. For example, although some aspects of have been described with reference to a flowchart, those skilled in the art should readily appreciate that functions, operations, decisions, etc. of all or a portion of each block, or a combination of blocks, of the flowchart may be combined, separated into separate operations or performed in other orders. Moreover, while the embodiments are described in connection with various illustrative structures, one skilled in the art will recognize that the system may be embodied using a variety of data structures. For example, a fiber-optic splitter or coupler can be realized in a variety of ways, including one employing optical fibers the cores of which are positioned in close proximity and that exchange light via evanescent coupling. As another example, while embodiments of FIGS. 1 and 2A, 2B are shown to employ fiber-optic elements (optical fibers and fiber-optic couplers), a related embodiment of the optical imaging system may include an outer and/or inner nested interferometers at least a portion of at least one of which is implemented using free-space propagation optical schemes and/or beam-splitters that include a conventional reflector.

In a related embodiment, the implementation of a nested interferometer may differ from that of FIGS. 1 and 2A. For example, a shearing interferometer (with or without an air-gap), Sagnac interferometer, or Michelson interferometer or another optical component configured to cause a double reflection in an arm of the outer interferometer can generally be employed, to name just a few, to achieve sought after results. Furthermore, such optical component can also be disposed in a reference arm of the outer interferometer. The use of embodiments (in particular, the switching between the branches of discussed interferometric setups) may require adjustment of phase and/or the use of phase stabilization arrangement and/or appropriate data processing to compensate for such phase shifts.

An alternative embodiment can be implemented with the use of a double-reflector in an arm of the outer interferometer (such as a polarization-sensitive partially-reflective partially-transmissive layer on a surface of the mirror). When the polarization state of light reflected off from the mirror is perpendicular to the polarization state defined by the polarization-sensitive layer, the only reflection delivered to the arm of the interferometer is that from the polarization-sensitive layer. In this case, no nested or inner interferometer is required. In another implementation, a birefringent medium or a component adapted to vary optical dispersion can be made a part of an arm of the interferometer. For example, when a birefringent medium is disposed in the sample arm, such medium causes different optical and/or time delays for light of different polarizations reflected off from a common location (an interface) within the sample. Thus, to name but a few, it is contemplated that the present invention can utilize a double reflection off the grating, two paths through the lens, a beam splitter and mirror in a delay line, a birefringent element in either arm of an interferometer, or a double grating to cause a photon pair to self interfere.

In addition, it is appreciated that while the examples of use of embodiments were discussed in reference to differentiation between a lipid-containing and substantially lipid-free samples, embodiments of the invention are generally adapted to assess the a material characteristic of the interrogated sample. Furthermore, it is realized that in a related embodiment the subtraction of optical data corresponding to different scans of the sample can be implemented by employing an array of detectors (instead of the detection system operating an a dual mode) and processing the acquired analog data, with hardware and not with software. If implemented, such approach will not require actual digital subtraction of one of the data sets from another. Finally, disclosed aspects, or portions of these aspects, may be combined in ways not listed above. Accordingly, the invention should not be viewed as being limited to the disclosed embodiment(s).

What is claimed is:

1. A device for characterizing an object, the device comprising:
    at least one light source configured to direct photons toward an object;
    an interferometer configured to receive photons from the object;
    at least one detector system configured to detect an optical signal at an output of the interferometer and to remove, from said optical signal, a signal portion representing first order photon correlations, when present; and
    a processor configured to receive data relating to second-order correlated photons from said at least one detector system,
    wherein each photon or photon pair is subject to at least two indistinguishable paths to a photon or photon pair but differing in at least one of time and length, and
    wherein the processor is configured to characterize the object based on a self interference of the second-order correlated photons from a common location within the object.

2. A device according to claim 1, wherein the processor is further configured to generate a profile of second-order correlations (SOC) of light from the common location within the object, said profile being indicative of a material characteristic of the object.

3. A device according to claim 1, wherein the at least one light source is configured to direct photons toward the object through an optically-misbalanced interferometer nested in an arm of said interferometer.

4. A device according to claim 1, wherein the at least one detector system includes at least one of (i) an optical detection system configured to operate in a single-channel detection mode and a dual-channel balanced detection mode and (ii) multiple optical detectors.

5. A device according to claim 1, wherein the interferometer includes, in an arm thereof, at least one of (i) a varying optical delay line, (ii) a varying time delay line, (iii) a fixed optical group delay line, (iv) a diffraction grating, (v) a second optically-misbalanced interferometer, (vi) an element configured to vary polarization of light, (vii) a birefringent medium, and (viii) an element producing a double reflection of light.

6. A device according to claim 1, wherein the at least one light source includes a non-quantum source of light.

7. A device according to claim 1, wherein the at least one light source includes at least one of (a) a swept source and (b) a source having an output that is swept and thereby configured to sweep across a predetermined bandwidth.

8. A device according to claim 1, wherein the processor is configured to perform data processing in a Fourier domain to characterize the object.

9. A method for determining a material characteristic of an object with the use of an optical system including (i) a first interferometer having input, output, and first and second arms, (ii) a second interferometer in an arm of the first interferometer, and (iii) a detector system configured to operate in a single-channel and dual-channel balanced detector modes and configured in optical communication with the output, the object being in the second arm, the method comprising:
    illuminating the object with incident light through the second arm;
    receiving, with said detector system configured to operate in the single-channel detector mode, incident light from the second interferometer that has reflected from the object to acquire first data representing an optical scan of the sample;
    receiving, with said detector system configured to operate in the dual-channel detector mode, incident light from the second interferometer that has reflected from the object to acquire second data representing an optical scan of the sample, and
    processing, in a computer process, said first and second data to derive second-order correlations data representing a material characteristic of the sample.

10. A method according to claim 9, further comprising imaging the object to identify a reflective interface thereof.

11. A method according to claim 9, wherein said processing includes subtracting the second data from the first data.

12. A method according to claim 9, further comprising plotting said second-order correlations data as a function of at least one of a position inside the object and a position across the object to form a plot representative of said material characteristic of the object.

13. A method according to claim 9, wherein said material characteristic includes an indication of at least one of presence of lipid material in said object and a lack of presence of lipid material in said object.

14. A method according to claim 9, wherein any of said receiving incident light with said detector system configured to operate in the single-channel detector mode and receiving incident light with said detector system configured to operate in the dual-channel detector mode includes receiving light from the first arm of said first interferometer.

15. A method according to claim 9, wherein any of said receiving incident light with said detector system configured to operate in the single-channel detector mode and receiving incident light with said detector system configured to operate in the dual-channel detector mode includes receiving light from an optical delay line configured to operate to modify optical dispersion in an arm of the first interferometer.

16. A method according to claim 15, wherein at least one of the first and second interferometers is configured to generate an interferogram, and further comprising operating said optical delay line to modify said optical dispersion to induce chirp in the interferogram.

17. A method according to claim 9, wherein said illuminating includes illuminating the object with light from at least one laser source of light that is in optical communication with the input of the first interferometer.

18. A method according to claim 9, wherein said illuminating includes illuminating the object with light from a thermal source of light that is in optical communication with the input of the first interferometer.

19. A method according to claim 9, wherein said illuminating includes illuminating the object with light from the second interferometer.

20. A method for determining a presence of a constituent material in an object, the method comprising:
    illuminating the object with light from a source of light optically coupled to a first interferometer, the first interferometer having:
        input and output;
        a sample arm; and
        a second interferometer as part of the sample arm,
    receiving, with a detector system configured to operate in a single-channel detector mode, light including incident light that has reflected from the object and traversed the second interferometer to acquire a first set of interferometric data;

receiving, with said detector system configured to operate in a dual-channel detector mode, light including said incident light that has reflected from the object and traversed the second interferometer to acquire a second set of interferometric data; and subtracting the second set of data from the first set of data to determine second-order correlations (SOC) data indicating at least one constituent material of the object.

21. A method according to claim 20, further comprising changing optical dispersion in an arm of the first interferometer.

22. A method according to claim 21, wherein said changing optical dispersion includes changing optical dispersion in an arm of the first interferometer.

23. A method according to claim 20, further comprising plotting said SOC data as a function of depth of the object to form an SOC plot.

24. A method according to claim 20, wherein said constituent material of the object includes at least one of lipid and intravascular plaque.

25. An optical imaging system comprising:
an outer interferometer having input and output;
an inner interferometer nested within the outer interferometer, the inner interferometer defining unequal first and second optical paths through the inner interferometer;
an optical detection system coupled to the output of the outer interferometer and configured to detect an interferogram formed at said output when light is coupled into the input of the outer interferometer;
a source of light in optical communication with said input; and
a processor configured to receive imaging data corresponding to a detected interferogram and calculate, from said imaging data, data representing a quantum mechanical characteristic of light at said output,
wherein said quantum mechanical characteristic includes a second-order correlations (SOC) characteristic of light.

26. An optical imaging system according to claim 25, wherein said optical detection system is configured to operate both as a single-channel detection system and as a dual-channel balanced detection system.

27. An optical imaging system according to claim 25, wherein the inner interferometer is part of a sample arm of the outer interferometer.

28. An optical imaging system according to claim 25, configured to optically interrogate an object in a sample arm of the outer interferometer, the object including a surface and a material disposed thereon, wherein said processor is further configured to generate a user-perceivable indicator indicating a characteristic of the material.

29. An optical imaging system according to claim 28, wherein said processor is configured to generate a plot of the SOC characteristic of light that has been delivered to the sample from the source when the source of light and reflected by the sample through the inner interferometer towards the optical detection system, said source of light including a pseudo-thermal source of light.

30. An optical imaging system according to claim 25, configured to operate as at least one of low-coherence interferometric (LCI) system and optical coherence tomography (OCT) system.

31. An optical imaging system according to claim 30, further comprising an optical switch configured to enable and operation of the optical imaging system as the at least one of the LCI and OCT system.

* * * * *